United States Patent [19]

Macdonell et al.

[11] Patent Number: 4,700,004
[45] Date of Patent: Oct. 13, 1987

[54] CONVERSION OF MERCAPTANS TO DISULFIDES WITH SOLUBLE COBALT CATALYST SYSTEM

[75] Inventors: Gary D. Macdonell; Donald H. Kubicek, both of Bartlesville, Okla.

[73] Assignee: Phillips Petroleum Company, Bartlesville, Okla.

[21] Appl. No.: 586,610

[22] Filed: Mar. 6, 1984

Related U.S. Application Data

[62] Division of Ser. No. 181,518, Aug. 26, 1980, abandoned.

[51] Int. Cl.$^4$ .......................................... C07D 149/00
[52] U.S. Cl. ................................................. 568/26
[58] Field of Search ................................... 568/21, 26

[56] References Cited

U.S. PATENT DOCUMENTS 3,565,959  2/1971  Takase et al. .......................... 568/26
4,277,623  7/1981  Kubicek ................................. 568/26

FOREIGN PATENT DOCUMENTS 1122889  8/1968  United Kingdom .

Primary Examiner—Donald G. Daus
Assistant Examiner—Cecilia Shen
Attorney, Agent, or Firm—A. W. Umphlett

[57] ABSTRACT

A catalyst system consisting essentially of a cobalt salt of a carboxylic acid, an alkali or alkaline earth metal hydroxide, and an alkanol is set forth and has been employed to oxidize a mercaptan to a disulfide.

15 Claims, No Drawings

CONVERSION OF MERCAPTANS TO DISULFIDES WITH SOLUBLE COBALT CATALYST SYSTEM

This is a divisional application of our copending application having Ser. No. 181,518, filed Aug. 26, 1980, now abandoned.

BRIEF DESCRIPTION OF INVENTION

A cobalt salt of a carboxylic acid, an alkali or alkaline earth metal hydroxide, and an alkanol form a soluble catalyst system useful to convert mercaptans to corresponding disulfides.

A DETAILED DESCRIPTION

This invention relates to the preparation of a disulfide. It also relates to the conversion of a mercaptan or thiol to a disulfide. Further it relates to a catalytic conversion of a mercaptan or thiol to a corresponding disulfide in the presence of a catalyst. In one of its aspects, the invention relates to the provision of a soluble cobalt catalyst system for the conversion of a mercaptan or thiol to a corresponding disulfide.

In one of its concepts, the invention provides a process for the conversion of a mercaptan to a corresponding disulfide which comprises oxidizing the mercaptan in the presence of a catalyst essentially comprising a cobalt salt or a carboxylic acid, an alkali or alkaline earth metal hydroxide and an alkanol. In another of its aspects, the invention provides a catalyst system in which a mercaptan is soluble and in which or with which it can be converted to a corresponding disulfide by oxidation with an oxygen-containing gas or oxygen, said catalyst comprising essentially a cobalt salt of a carboxylic acid, an alkali or alkaline earth metal hydroxide and an alkanol.

Organic disulfides have varied applications ranging from intermediates for insecticides, herbicides and rodent repellents to additives in greases and diesel fuels. The synthesis of such disulfides are well known and are generally based on the corresponding thiols (mercaptans). One such synthesis is reported in U.S. Pat. No. 3,565,959 (issued Feb. 23, 1971), wherein mercaptans are converted to disulfides in the presence of oxygen, aqueous sodium hydroxide and an aqueous base soluble catalyst such as cobalt phthalocyanine. The patent boils the catalyst of its invention to render it soluble in aqueous alkaline solution so that it can be used as a homogeneous catalyst. Another such synthesis is reported in U.S. Pat. No. 2,574,884, issued Nov. 13, 1951, wherein tertiary alkyl mercaptans are oxidized with oxygen to disulfides in the presence of insoluble alumina-based catalysts such as chromia, vanadia and iron oxide. Still another disulfide synthesis is reported in U.S. Pat. No. 2,517,934, issued Aug. 8, 1950, wherein a liquid comprised of a mercaptan, disulfide product and dissolved oxygen is circulated through a fixed catalyst bed of cupric chloride and the disulfide product continuously withdrawn. These methods of disulfide synthesis each have certain disadvantages. For example, U.S. Pat. No. 3,565,959 requires water to solubilize the catalyst and this in turn reduces its effectiveness since many mercaptans such as ethyl, propyl, and butyl mercaptan are not very miscible with water. Other art cited involves the use of heterogeneous catalysts which require additional handling as well as being difficult to make efficient reactant-catalyst contact in a stirred autoclave. The disclosures of the cited patents are incorporated herein by the reference to them. We have now discovered, as evidenced by information herein contained, that there can be produced, without boiling or other special treatment, a homogeneous or soluble catalyst comprising a cobalt salt from which catalyst the products obtained can be recovered without resorting to filtration or other complex operation. Thus, the disulfide formed or other product in the formation of which the catalyst has been employed can be recovered by simple distillation. Thus, the essence of the present invention is to provide a catalyst system that is soluble in the reaction media used for the disulfide synthesis, that can be readily removed or otherwise separated from the disulfide product by water washing or distillation, and that has increased catalyst activity.

It is an object of this invention to produce a disulfide. It is another object of this invention to convert a mercaptan (thiol) to a disulfide. It is a further object of the invention to provide a catalyst system which is homogeneously soluble with a mercaptan. A further object of the invention, still, is to provide a process for the conversion of a mercaptan to a disulfide by oxidizing the same, as with an oxygen-containing gas or oxygen, employing a soluble catalyst system comprising cobalt. Importantly, also, it is a primary object of the invention to facilitate handling of the catalyst as in charging to a reaction, e.g., the reaction herein discussed, and in working up the reaction mass to obtain products in other portions thereof. Another object of the invention is to provide a catalyst system which can be produced without boiling the same yet will be homogeneously soluble in the reaction mass, but, nevertheless, contains a cobalt salt. A further object still is to provide a catalyst which does not need to be filtered from the reaction mass and recovering product therefrom which can be separated therefrom as by simple distillation. Another object of the invention is to provide a homogeneous catalyst system containing a cobalt salt useful in reacting a mercaptan continuously to form a disulfide employing cobalt as a catalytic ingredient.

Other aspects, concepts, objects and the several advantages of the invention are apparent from a study of this disclosure and the claims.

According to the present invention, a mercaptan is converted or oxidized to a disulfide, as with oxygen, employing for the purpose a homogeneously soluble catalyst essentially comprised of a cobalt salt of a carboxylic acid, an alkali or alkaline earth metal hydroxide, and an alkanol.

Thiols (mercaptans) useful in this invention are those materials represented by the formula, RSH, wherein R can be any alkyl, cycloalkyl, or aryl radical having from one to twenty carbon atoms. In addition, R can contain functional groups within the mentioned radicals such as hydroxyl, ether, ester, etc., type groups. Exemplary of compounds corresponding to the general formula are methanethiol, ethanethiol, 1-propanethiol, 2-propanethiol (isopropyl mercaptan), 1-butanethiol, 2-butanethiol, 2-methyl-2-propanethiol, 1-hexanethiol, 1-dodecanethiol, 1-eicosanethiol, cyclohexanethiol, benzenethiol, 4-methylbenzenethiol, 3-mercaptopropionic acid, 4-mercaptobutyric acid, methylmercaptoacetate, methyl-3-mercaptopropionate, butyl-3-mercaptobutyrate, 2-mercaptoethanol, 4-mercaptobutanol, methyl 2-mercaptoethyl ether, ethyl 2-mercaptoethyl ether, and the like.

The catalyst system useful in this invention is essentially comprised of three components, namely, (1) a cobalt salt of a carboxylic acid, (2) an alkali or alkaline earth metal hydroxide, and (3) an alkanol. Although the cobalt salt is considered by itself to be an effective catalyst, it performs best in the presence of an alkali or alkaline earth metal hydroxide and even better with the cobalt salt and metal hydroxide dissolved in an alkanol.

Cobalt carboxylates useful in this invention are those materials represented by the formula, $(R_1COO)_2Co$, wherein $R_1$ can be any alkyl, cycloalkyl or aryl radical having from one to twenty carbon atoms. Materials corresponding to the above general formula are, for example, but not limited to such compounds as cobalt acetate, cobalt propionate, cobalt 2-ethylhexanoate, cobalt dodecanoate, cobalt eicosanoate, cobalt nephthenate, cobalt cyclohexane carboxylate, cobalt benzoate, and the like.

The amount of cobalt salt employed can be broadly from about 0.001 weight percent to about 1 weight percent, preferably 0.005 weight percent to 0.1 weight percent based on the amount of mercaptan present.

Alkali or alkaline earth metal hydroxides useful in this invention are those hydroxides of metals found in Groups IA and IIA of the Periodic Table. The preferred metals are sodium or potassium. The amount of metal hydroxide used can be broadly from about 0.01 weight percent to about 10 weight percent, preferably 0.1 weight percent to 5 weight percent based on the amount of mercaptan used.

Alkanols useful in this invention are those liquids that have from one to six carbon atoms and boil below the particular disulfide product being prepared for easier separation by distillation. Such liquids can be methyl alcohol, ethyl alcohol, isopropyl alcohol, butyl alcohol, and hexyl alcohol with methyl alcohol being the most preferred. The amount of alcohol employed can be whatever is sufficient to dissolve the metal hydroxide being used. Inert solvents such as hydrocarbons can also be employed as co-solvents but are generally not needed since the alcohol can also serve as the solvent.

The reaction can be carried out from about 15° C. to about 100° C., preferably 21° C. (70° F.) to 55° C. (130° F.). The pressure can be from about 0 psig to about 1000 psig, preferably 100 psig to 500 psig. Oxygen or any mixture of oxygen and inert gas such as air can be employed and can be introduced into the liquid or vapor phase of the reaction. Any type reactor, batch or continuous, can be employed. The reaction conditions, reactors, etc., will vary depending on the particular need so that these parameters are left to those skilled in the art.

The following examples serve to illustrate the operability of this invention.

EXAMPLE I

This example is a control to illustrate reaction conditions and yield in preparing a disulfide from the corresponding mercaptan using a heterogeneous catalyst system. Into a 300 milliliter stainless steel reactor equipped with a stirrer, thermocouple, back-pressure regulator, gas inlet tube, electric heater and cooling coils was added 2 grams of sodium hydroxide dissolved in 6 grams of water, 0.4 gram of HDS-2 catalyst (cobalt molybdate on alumina, a hydrodesulfurization catalyst from American Cyanamid), 36 grams of isopropyl alcohol and 80.9 grams (1.062 moles) of isopropyl mercaptan. The reactor was closed and the stirrer started while the contents were slowly heated to 54° C. (130° F.) and the system pressured with nitrogen to 220 psig. Oxygen, 25 psig, was added and maintained at that level during the run while the temperature was controlled between 54°-57° C. (130°-135° F.) with either heating or cooling. Completion of the reaction was noted (2.5 hours) by the need for heat to maintain the desired temperature and the lack of an oxygen pressure drop. The reactor was cooled, vented and the top layer analyzed by GLC on a 365 cm (12 ft.)×0.635 cm (0.25 in.) column packed with 10 percent SE 30 silicone rubber on 60-80 mesh Chromosorb P that had been previously mineral acid washed and dried. There was obtained a 100 percent conversion of the mercaptan to a product having a yield and selectivity of 97.7 percent diisopropyl disulfide.

EXAMPLE II

This example describes an inventive run wherein a soluble cobalt catalyst was employed along with the alkali metal hydroxide and alkanol. The results show the conversion, yield and selectivity are comparable to those disclosed in Example I even though the size of the run was about 200 times larger than that described in Example I. The length of the larger run was about the same as for the smaller run of Example I suggesting the increased activity of the inventive catalyst. The disulfide yield was slightly lower in the larger run than in the smaller run but the yield of the larger run was a distilled product yield whereas with the smaller run the product yield was based on GLC analysis which may account for the difference. A 10-gallon reactor equipped as described in Example I was charged with 0.9 pound of sodium hydroxide, 17.2 pounds of methyl alcohol, 10 grams of a 6 weight percent cobalt naphthenate solution and 35.5 pounds (0.467 pound mole) of isopropoyl mercaptan. The reaction was conducted in the same manner as described in Example I except 300 psig air was maintained on the system throughout the run. After the run was complete (2.7 hours), the product effluent was removed and distilled. A 91.4 weight percent yield of diisopropyl disulfide (100 percent mercaptan conversion) was obtained distilling at about 112° C./100 Torr. (mm).

EXAMPLE III

This example is a control illustrating the yield, mercaptan conversion and reaction conditions obtained when an inorganic homogeneous catalyst system is employed in the conversion of cyclohexyl mercaptan to dicyclohexyl disulfide. The procedure described in Example I was essentially repeated except the charge was 47.5 grams (0.409 mole) of cyclohexyl mercaptan, 19.8 grams of methyl alcohol and 1 gram of solid sodium hydroxide. The reactor was first pressured to 200 psig with nitrogen and then to 300 psig with oxygen. The run was completed in 2 hours and analyzed by GLC. A 77.4 percent conversion of mercaptan was obtained with a 100 percent selectivity to dicyclohexyl disulfide (76.8 mole percent yield).

EXAMPLE IV

This example is of inventive runs illustrating the enhanced activity of adding a soluble cobalt-containing compound to the synthesis described in Example III. The charge and procedure described in Example III was repeated except 0.01 gram of cobalt 2-ethylhexanoate was added. The run, IVa, was complete in 0.75 hour with a 99.5 percent cyclohexyl mercaptan conversion and a 100 percent disulfide selectivity giving a 99.5 mole percent yield of dicyclohexyl disulfide. The reaction describing the use of cobalt 2-ethylhexanoate, methyl alcohol, and sodium hydroxide was repeated (Run IV(b)), on a larger scale (373X) involving a charge of 5 grams of cobalt 2-ethylhexanoate, 39.1 pounds cyclohexyl mercaptan, 0.9 pound of-sodium hydroxide and 15.85 pounds of methyl alcohol. A 100 percent conversion of cyclohexyl mercaptan was obtained after one hour of reaction time giving 100 percent disulfide selectivity. The effluent was diluted with 2.5 gallons of water, stirred 30 minutes at about 25° C. and the oil phase separated. The oil phase was then heated to about 116° C. while nitrogen was bubbled through at 6 scfh at one atmosphere pressure for 4 hours. There was obtained 34.45 pounds (93.4 mole percent yield) of essentially pure dicyclohexyl disulfide.

EXAMPLE V

This example is an inventive run illustrating the use of another soluble cobalt-containing catalyst system. The run also suggests that because of the enhanced catalyst activity of the cobalt-containing catalyst system, the reaction can be operated with less alcohol present. Into a 300 milliliter stainless steel reactor equipped as described in Example I was charged 12 grams of methyl alcohol, 2 grams of sodium hydroxide, 0.1 gram of cobalt acetate and 86 grams (0.74) moles of cyclohexyl mercaptan. The reactor was pressured to 240 psig with nitrogen, heated to 55° C. (131° F.) and then pressured to 300 psig with oxygen. The reaction was complete in 3 hours. The effluent was water washed and the oil layer dried on a Rotovap at 90°-100° C./20-40 Torr. (mm) to give a 100 percent selectivity and 83.8 percent yield of dicyclohexyl disulfide.

The reactions described herein are summarized in Table I wherein it is shown that in general the inventive homogeneous catalyst systems based on a cobalt salt of an organic acid, an alkali metal hydroxide and an alcohol (Examples II, IV and V) give higher yields of disulfides from mercaptans, higher mercaptan conversions and allow faster reaction times than do some other inorganic homogeneous catalyst systems (Example III) and heterogeneous cobalt-containing catalyst systems (Example I).

It is evident from the foregoing disclosure and examples that there have been provided a catalyst system which is readily handled to produce the desired reaction. Also the reaction mass can be worked off, as by distillation, to recover products and other materials therefrom without any complex operation such as filtration having to be applied. The fact that the catalyst is homogeneous and soluble renders it applicable in a number of reactions in which cobalt catalyst is useful.

The catalyst system described herein may possibly be used in other oxidations such as the oxidation of hydrocarbons to carboxylic acids, alcohols, aldehydes, and ketones.

TABLE
SUMMARY

| Example No. | Ingredients | | | | Reaction Conditions | | | Results | | |
|---|---|---|---|---|---|---|---|---|---|---|
| | Catalyst | Mercaptan | NaOH | CH₃OH | Temp., °F. | Press., psig | Time, Hrs. | % RSH Conv. | %-SS-Sel. | %-SS-Yield |
| I | Cobalt Molybdate[a] (0.4 g) | Isopropyl-SH, 80.9 g | 2[b] g | 36[c] g | 130 | 220 (N₂) 25 (O₂) | 2.5 | 100 | 97.7 | 97.7 |
| II | Cobalt Naphthenate[d] | Isopropyl-SH 35.5 lbs. | 0.9 lbs. | 17.2 lbs. | 130 | 300 (air) | 2.7 | 100 | — | 91.4 |
| III | No catalyst used | Cyclohexyl-SH, 47.5 g | 1 g | 19.8 g | 135 | 200 (N₂) 100 (O₂) | 2 | 77.4 | 100 | 76.8 |
| IVa | Cobalt 2-Ethyl-hexanoate, (0.1 g) | Cyclohexyl-SH, 47.5 g | 1 g | 19.8 g | 144 | 200 (N₂) 100 (OH₂) | 0.7 | 99.5 | 100 | 99.5 |
| b | Cobalt 2-Ethyl-hexanoate (5 g) | Cyclohexyl-SH, 39.1 lbs. | 0.9 lbs. | 15.85 lbs. | 150 | 280 (N₂) 60 (O₂) | 1 | 100 | 100 | 93.4 |
| V | Cobalt Acetate (0.1 g) | Cyclohexyl-SH, 86 g | 2 g | 12 g | 130 | 240 (N₂) 60 (O₂) | 3 | — | 100 | 83.8 |

[a]HDS-2 from American Cyanamid (3–4 wt. % cobalt oxide, 15–16 wt. % molybdenum oxide).
[b]Also present 6 grams water.
[c]Isopropyl alcohol employed.
[d]6 wt. % cobalt naphthenate in solution.

Reasonable variation and modification are possible within the scope of the foregoing disclosure and the appended claims to the invention, the essence of which is that there has been set forth a catalyst system comprising essentially a cobalt salt of a carboxylic acid, an alkali or alkaline earth metal hydroxide, and an alcohol; and that the catalyst has been found to be eminently useful to oxidize a mercaptan to a disulfide, as described.

We claim:

1. A process for the conversion of a mercaptan to the corresponding disulfide which comprises contacting under oxidizing conditions (1) oxygen and (2) a reaction mixture consisting essentially of (a) the mercaptan and (b) a homogeneous catalyst system soluble in said reaction mixture said catalyst system consisting of a cobalt salt of a carboxylic acid, an alkali or alakaline earth metal hydroxide and an alkanol.

2. A process according to claim 1 wherein the cobalt salt of the carboxylic acid is represented by the formula $(R_1COO)_2$ Co wherein $R_1$ can be an alkyl, cycloalkyl or aryl radical having from one to twenty carbon atoms.

3. A process according to claim 2 wherein the cobalt salt is at least one of the following: cobalt acetate cobalt propionate, cobalt 2-ethylhexanoate, cobalt dodecanoate, cobalt eicosanoate, cobalt naphthenate, cobalt cyclohexane carboxylate and cobalt benzoate.

4. A process according to claim 1 wherein the alkanol is at least one selected from the following: methyl, ethyl, isopropyl, butyl, and hexyl alcohols.

5. A process according to claim 1 wherein the alkali metal hydroxide is at least one of sodium and potassium hydroxides.

6. A process for the oxidation of a mercaptan to a disulfide which comprises
   contacting under oxidizing conditions (1) oxygen and (2) a reaction mixture consisting essentially of (a) a mercaptan and (b) a homogeneous catalyst system soluble in said reaction mixture said catalyst system consisting of a cobalt salt of a carboxylic acid, an alkali or alkaline earth metal hydroxide and an alkanol wherein the amount of cobalt employed is in the approximate range of from about 0.001 to about 1 weight percent based on the amount of mercaptan present and wherein the amount of hydroxide is in the approximate range of from about 0.01 weight percent to about 10 weight percent based on the amount of mercaptan present.

7. A process according to claim 6 wherein the oxidation is effected at a temperature in the range of from about 15° C. to about 100° C. and wherein a pressure of oxygen in the approximate range of from about 0 to about 1000 psig is applied to the reaction mass.

8. A process according to claim 6 wherein said mercaptan is isopropyl mercaptan.

9. A process according to claim 6 wherein said mercaptan is cyclohexyl mercaptan.

10. A process according to claim 6 wherein the cobalt salt of the carboxylic acid is represented by the formula $(R_1COO)_2 Co$ where $R_1$ can be an alkyl, cycloalkyl or aryl radical having from one to twenty carbon atoms.

11. A process according to claim 6 wherein said hydroxide is an alkali metal hydroxide.

12. A process according to claim 6 wherein said alkanol contains from 1 to 6 atoms.

13. A process according to claim 6 wherein said cobalt salt is one of cobalt acetate, cobalt propionate, cobalt 2-ethylhexanoate, and cobalt naphthenate, said hydroxide is sodium hydroxide and said alkanol is methanol.

14. A process accoding to claim 8 wherein said cobalt salt is cobalt naphthenate, said hydroxide is sodium hydroxide, and said alkanol is methanol.

15. A process according to claim 9 wherein said cobalt salt is cobalt acetate, said carboxylic acid is cobalt 2-ethylhexanoate, said hydroxide is sodium hydroxide, and said alkanol is methanol.

* * * * *

UNITED STATES PATENT AND TRADEMARK OFFICE
CERTIFICATE OF CORRECTION

PATENT NO. : 4,700,004

DATED : OCTOBER 13, 1987

INVENTOR(S) : GARY D. MacDONALD; DONALD H. KUBICEK

It is certified that error appears in the above-identified patent and that said Letters Patent is hereby corrected as shown below:

Claim 12, column 8, line 8, after "from 1 to 6" there should be inserted "carbon"

Signed and Sealed this

Twenty-first Day of June, 1988

Attest:

DONALD J. QUIGG

Attesting Officer

Commissioner of Patents and Trademarks